US010556077B2

(12) United States Patent
Avitsian et al.

(10) Patent No.: US 10,556,077 B2
(45) Date of Patent: Feb. 11, 2020

(54) REVERSIBLE AIRWAY DEVICE AND RELATED METHOD FOR VENTILATING A SUBJECT

(71) Applicant: THE CLEVELAND CLINIC FOUNDATION, Cleveland, OH (US)

(72) Inventors: Rafi Avitsian, Solon, OH (US); Andrew Zura, Broadview Hts., OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 505 days.

(21) Appl. No.: 14/048,343

(22) Filed: Oct. 8, 2013

(65) Prior Publication Data
US 2014/0096766 A1    Apr. 10, 2014

Related U.S. Application Data

(60) Provisional application No. 61/710,810, filed on Oct. 8, 2012.

(51) Int. Cl.
*A61M 16/04*    (2006.01)

(52) U.S. Cl.
CPC ..... *A61M 16/0488* (2013.01); *A61M 16/0434* (2013.01)

(58) Field of Classification Search
CPC ............... A61B 1/00135; A61B 1/267; A61M 16/0084; A61M 16/04; A61M 16/0409;
(Continued)

(56) References Cited

U.S. PATENT DOCUMENTS 4,334,534 A *  6/1982  Ozaki ................... A61M 16/04
                                                  128/207.15
5,174,283 A * 12/1992  Parker .............. A61M 16/0488
                                                  128/200.26
(Continued)

FOREIGN PATENT DOCUMENTS

CN        1051511 A      8/1990
CN        1051511 A      5/1991
(Continued)

OTHER PUBLICATIONS

PCT Communication Relating to the Results of the Partial International Search, dated Jan. 29, 2014, pp. 5-6.
(Continued)

*Primary Examiner* — Bradley H Philips
*Assistant Examiner* — Victoria Murphy
(74) *Attorney, Agent, or Firm* — Tarolli, Sundheim, Covell & Tummino LLP

(57) ABSTRACT

One aspect of the present disclosure relates to a reversible airway device that includes a tubular guide, a laryngeal mask, an endotracheal tube, and a sealing mechanism. The tubular guide can have a distal end portion, a proximal end portion, and a first passageway extending between the distal and proximal end portions. The laryngeal mask can be attached to the distal end portion of the tubular guide. The laryngeal mask can include an opening in fluid communication with the first passageway. The endotracheal tube can be slidably disposed within the first passageway and have a second passageway that is concentric with the first passageway. The sealing mechanism can be disposed within the first passageway and be configured to occlude the flow of a gas through the first passageway.

22 Claims, 9 Drawing Sheets

(58) Field of Classification Search
CPC .......... A61M 16/0415; A61M 16/0418; A61M 16/0434; A61M 16/0445; A61M 16/0488; A61M 16/0493; A61M 16/06; A61M 16/08

See application file for complete search history.

(56) References Cited

U.S. PATENT DOCUMENTS

| | | | |
|---|---|---|---|
| 5,339,808 A | 8/1994 | Don Michael | |
| 5,477,851 A | 12/1995 | Callaghan et al. | |
| 5,660,175 A * | 8/1997 | Dayal | A61M 16/00 128/207.15 |
| 6,070,581 A * | 6/2000 | Augustine | A61B 1/267 128/200.26 |
| 6,079,409 A | 6/2000 | Brain | |
| 6,634,354 B2 * | 10/2003 | Christopher | A61M 16/0488 128/200.26 |
| 7,040,312 B2 * | 5/2006 | Alfery | A61M 16/0409 128/200.26 |
| 7,128,071 B2 * | 10/2006 | Brain | A61M 16/04 128/200.26 |
| 7,174,889 B2 * | 2/2007 | Boedeker | A61M 16/04 128/200.26 |
| 7,938,118 B2 * | 5/2011 | Kessler | A61M 16/04 128/200.26 |
| 8,887,716 B2 * | 11/2014 | Dubach | A61M 16/04 128/200.26 |
| 2001/0032646 A1 | 10/2001 | Christopher | |
| 2005/0051175 A1 | 3/2005 | Brain | |
| 2005/0081861 A1 * | 4/2005 | Nasir | A61M 16/04 128/207.14 |
| 2005/0139220 A1 | 6/2005 | Christopher | |
| 2005/0268917 A1 * | 12/2005 | Boedeker | A61M 16/04 128/207.14 |
| 2008/0257356 A1 | 10/2008 | Swick | |
| 2009/0090356 A1 * | 4/2009 | Cook | A61M 16/04 128/200.26 |
| 2012/0090609 A1 * | 4/2012 | Dubach | A61M 16/04 128/204.18 |
| 2014/0228640 A1 * | 8/2014 | Breslauer | A61M 16/04 600/115 |
| 2015/0165148 A1 | 6/2015 | Kozlowski et al. | |

FOREIGN PATENT DOCUMENTS

| | | |
|---|---|---|
| EP | 0500778 B1 | 2/1997 |
| GB | 2472063 A | 1/2011 |
| JP | 10314308 A | 12/1998 |
| JP | 5501660 A | 12/2010 |
| WO | 9107201 A1 | 5/1991 |
| WO | 2009025843 A1 | 2/2009 |
| WO | 2012127435 A1 | 9/2012 |

OTHER PUBLICATIONS

PCT Invitation to Pay Additional Fees for PCT/US2015/039858, dated Oct. 13, 2015, pp. 1-6.
International Search Report and Written Opinion for PCT/US2015/039858, dated Jan. 7, 2016, pp. 1-19.
Office Action for corresponding CN Application No. 201380063063.5, dated Jun. 8, 2017, 3 pages.
Search Report for corresponding CN Patent Application No. 201380063063.5, dated Apr. 27, 2017.
Office Action for corresponding Japanese Patent App. No. 2015-536831, dated Jan. 31, 2017, pp. 1-2.
Office Action for corresponding Chinese Patent App. No. 201380063063.5, dated Dec. 5, 2016, pp. 1-7.
Patent Office of the People's Republic of China Search Report for Application No. 2013800630635, pp. 1-2.
Japanese Office Action for corresponding Japanese Application No. 2015-536831, dated Dec. 5, 2017, pp. 1-4.

* cited by examiner

US 10,556,077 B2

REVERSIBLE AIRWAY DEVICE AND RELATED METHOD FOR VENTILATING A SUBJECT

RELATED APPLICATION

The present application claims the benefit of U.S. Provisional Patent Application Ser. No. 61/710,810, filed Oct. 8, 2012, the entirety of which is hereby incorporated by reference for all purposes.

TECHNICAL FIELD

The present disclosure relates generally to the field of anesthesiology and, more particularly, to a reversible airway device and related method for ventilating a subject using the airway device that does not risk disconnection or loss of the patient's airway during ventilation.

BACKGROUND

Airway devices are widely used in hospital surgical environments to provide respiratory assistance and ventilate patents during medical procedures. While there are a multitude of airway devices currently on the market, one popular airway device is an endotracheal tube and another is a supra-glottic support device, such as a laryngeal mask airway (LMA). While the use of these devices is widespread, there are disadvantages associated with each of these devices.

Endotracheal tubes, for example, are used to ventilate patients requiring anesthesia and/or respiratory assistance. An example of a conventional endotracheal tube is a plastic tube, which is inserted into a subject's mouth, passed down the trachea through the vocal cords, and lodged in the trachea proximal (or above) the lungs. The endotracheal tube may have a cuff or balloon portion surrounding the circumference of the endotracheal tube near the distal end that rests in the subject's trachea. After the endotracheal tube has been inserted properly, the cuff may be inflated to seal against the wall of the trachea. Once sealed, positive pressure ventilation may be used to provide respiratory assistance and, if desired, anesthesia or other gas, gas mix, etc., to the patient though the endotracheal tube via a ventilator. The cuff provides a seal that tends to block liquids and solids from passing along the outside of the endotracheal tube between the tube and the trachea wall and entering the subject's lungs.

A LMA typically includes a hollow tube (sometimes referred to as a tubular guide, tube or guide) and a laryngeal mask. The laryngeal mask of the LMA is intended to fit in the mouth of a patient and to cover the two openings leading, respectively, to the esophagus and the trachea, on the one hand, and blocking the fluid path to and from the esophagus and stomach, on the other hand, thereby providing a fluid path to the trachea and lungs for ventilating the patient. The laryngeal mask may be positioned without requiring a physician to view the airway directly. The laryngeal mask has an inflatable cuff or rim area. Once the laryngeal mask is placed into the subject's mouth, the cuff can be inflated to seal against the walls of the inside of the mouth and, if positioned properly, to block flow to and from the esophagus. A flexible, membranous support material extends from the cuff to form a recessed area, e.g., a space or volume, into which a gas mix can be pumped through the tube or other instrumentality of the LMA to provide the requisite air and/or anesthesia to the patient. The tube is of relatively large diameter, as compared to the usually relatively narrower diameter passage of a conventional endotracheal tube, and such relatively large diameter facilitates gas mix and exhalant flow with relatively minimal interference, pressure drop, etc. The support material supports the cuff from the tube. Thus, the LMA can be used to supply a gas mix to the recessed area and from there to the trachea.

In patients that require ventilation with an airway device (e.g., critically ill or injured subjects), it is important to maintain a continuous airway. In such patients, if ventilation begins with a supra-glottic support device (e.g., a LMA) and intubation subsequently becomes necessary, the supra-glottic support device must be removed from the patient so that an endotracheal tube can be placed. Doing so, however, requires that the patient's airway be temporarily disrupted while also increasing the risk that the patient's airway may not be recovered. Additionally, placing an endotracheal tube requires the skill of an experienced medical professional, who may not be present in all circumstances in which unexpected intubation is required.

SUMMARY

The present disclosure relates generally to the field of anesthesiology and, more particularly, to a reversible airway device and related method for ventilating a subject using the airway device that does not risk disconnection or loss of the patient's airway during ventilation.

One aspect of the present disclosure relates to a reversible airway device that includes a tubular guide, a laryngeal mask, an endotracheal tube, and a sealing mechanism. The tubular guide can have a distal end portion, a proximal end portion, and a first passageway extending between the distal and proximal end portions. The laryngeal mask can be attached to the distal end portion of the tubular guide. The laryngeal mask can include an opening in fluid communication with the first passageway. The endotracheal tube can be slidably disposed within the first passageway and have a second passageway that is concentric with the first passageway. The sealing mechanism can be disposed within the first passageway and be configured to occlude the flow of a gas through the first passageway.

Another aspect of the present disclosure relates to a reversible airway device that includes a tubular guide, a laryngeal mask, an endotracheal tube, a sealing mechanism and a stiffening mechanism. The tubular guide can have a distal end portion, a proximal end portion, and a first passageway extending between the distal and proximal end portions. The laryngeal mask can be attached to the distal end portion of the tubular guide. The laryngeal mask can include an opening in fluid communication with the first passageway. The endotracheal tube can be slidably disposed within the first passageway and have a second passageway that is concentric with the first passageway. The sealing mechanism can be disposed within the first passageway and be configured to occlude the flow of a gas through the first passageway. The stiffening mechanism can be operably connected to the laryngeal mask. The stiffening mechanism can be for selectively adjusting the position of the laryngeal mask relative to the airway of a subject.

Another aspect of the present disclosure can include a method for providing an artificial airway in a subject. One step of the method can include providing a reversible airway device. The airway device can include a tubular guide, a laryngeal mask, an endotracheal tube, and a sealing mechanism. The tubular guide can have a distal end portion, a proximal end portion, and a first passageway extending between the distal and proximal end portions. The laryngeal mask can be attached to the distal end portion and include an opening in fluid communication with the first passageway. The endotracheal tube can be slidably disposed within the first passageway and have a second passageway that is concentric with the first passageway. The sealing mechanism can be disposed in the first passageway. Next, the laryngeal mask can be inserted into the subject so that an airtight seal is formed between the laryngeal mask and the airway of the subject. After inserting the laryngeal mask, the endotracheal tube can be deployed so that a distal end of the endotracheal tube is positioned below the vocal cords of the subject. The endotracheal tube can then be retracted so that the distal end of the endotracheal tube is positioned above the vocal cords. A flow of gas through the second passageway is uninterrupted during the inserting and deploying steps.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
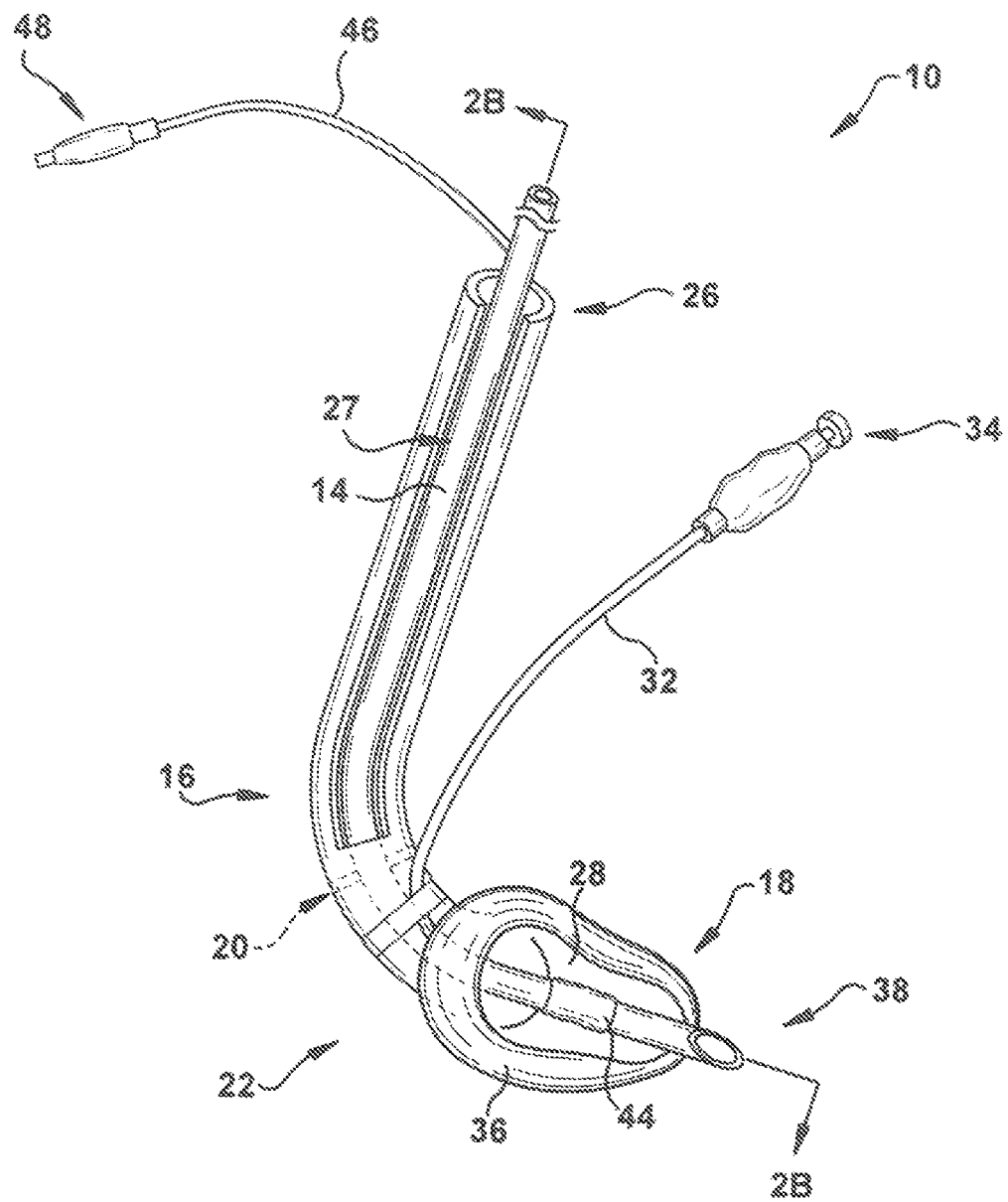
FIG. 1 is a perspective view of a reversible airway device constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "ventilating" or "ventilate" can refer to providing breathable air or oxygen, for example, and removing gas, etc., e.g., exhalant exhaled by a subject, and providing anesthesia and/or other materials to and/or from the lungs of a subject. The terms can also have the usual meaning as used in the field of medicine. The various gases, e.g., oxygen, air, anesthesia, etc., alone or in combination sometimes are referred to below collectively as a gas mixture.

As used herein, the terms "subject" and "patient" can be used interchangeably and refer to any warm-blooded organism including, but not limited to, human beings, pigs, rats, mice, dogs, goats, sheep, horses, monkeys, apes, rabbits, cattle, etc.

Overview

The present disclosure relates generally to the field of anesthesiology and, more particularly, to a reversible airway device and related method for ventilating a subject using the airway device that does not risk disconnection or loss of the patient's airway during ventilation. As representative of one aspect of the present disclosure, FIG. 1 illustrates a reversible airway device 10 for establishing an artificial airway and providing continuous ventilation in a subject when needed. Existing airway devices and associated methods for ventilating subjects involve the introduction of an endotracheal tube through a supra-glottic airway support device. This is time consuming, involves multiple devices, entails ventilation stoppage, and requires a high level of medical expertise. Advantageously, the present disclosure integrates both sub-glottic and supra-glottic support components that can easily and automatically provide intubation and, when needed, be quickly changed to function as a supra-glottic airway support while not compromising ventilation.

Reversible Airway Devices

One aspect of the present disclosure can include a reversible airway device 10. The reversible airway device 10 can generally include a supra-glottic airway support 12 (e.g., comprising a tubular guide 16 and a laryngeal mask 18), an endotracheal tube 14, and a sealing mechanism 20. By "reversible", it is meant that an artificial airway provided by the supra-glottic airway support 12 can be readily exchanged for an artificial airway provided by the endotracheal tube 14 without removing or disconnecting any component(s) of the airway device 10, and while maintaining continuous, uninterrupted ventilation. In other words, the term "reversible" can refer to the ability of the airway device 10 to be automatically changed from a supra-glottic airway support 12 to an endotracheal tube 14, and then back to a supra-glottic airway support, without compromising ventilation. As discussed in more detail below, the airway device 10 of the present disclosure can be used for all indications of a supra-glottic airway support device where there is a possibility that endotracheal intubation may be necessitated (e.g., in trauma or critically ill patients).

As shown in FIG. 1, one component of the airway device 10 includes a supra-glottic airway support 12. The supra-glottic airway support 12 can include a tubular guide 16 (e.g., a hollow tube) and a laryngeal mask 18 that surrounds, and is connected to, a distal end portion 22 of the tubular guide. The tubular guide 16 includes a first passageway (FIG. 2B) that extends between the distal end portion 22 (FIG. 1) and a proximal end portion 26 thereof. As discussed in more detail below, the first passageway 24 of the tubular guide 16 is sized and dimensioned to receive the endotracheal tube 14. Also partially extending between the proximal and distal end portions 26 and 22 of the tubular guide 16 is a longitudinal slot 27. The longitudinal slot 27 can serve as a rapid and convenient means for introducing the endotracheal tube 14 into the tubular guide 16. When in use, the proximal end portion 26 of the tubular guide 16 remains outside of the subject's mouth and, therefore, is accessible to a healthcare provider (e.g., physician, nurse or other individual). The proximal end portion 26 of the tubular guide 16 may be conveniently of any size and shape to secure a variety of attachments (not shown) to the tubular guide (e.g., a syringe, an endoscope probe, a gas mix supply connection to receive a gas mix for ventilating, anesthetizing, etc., a patient, a drainage tube, etc.).

Typically, the size and shape of the tubular guide 16 are selected so that the distal end portion 22 can be readily inserted into a subject's mouth and upper airway with the laryngeal mask 18 substantially sealing the laryngeal inlet of the subject. The tubular guide 16 is generally J-shaped to follow the profile of a typical subject's airway through the mouth, over the tongue, and into the laryngopharynx region of the subject just above the opening to the larynx. The tubular guide 16 is shaped to prevent the subject's tongue and pharynx from obstructing access to the trachea. The tubular guide 16 can be made from one or a combination of materials, such as plastic, with sufficient strength and rigidity to keep the subject's teeth apart and to prevent the subject from biting down and collapsing the tubular guide. The tubular guide 16 (as well as the laryngeal mask 18) can also be sized to accommodate a wide range of patient sizes (e.g., pediatric patients).

Figure 2A:
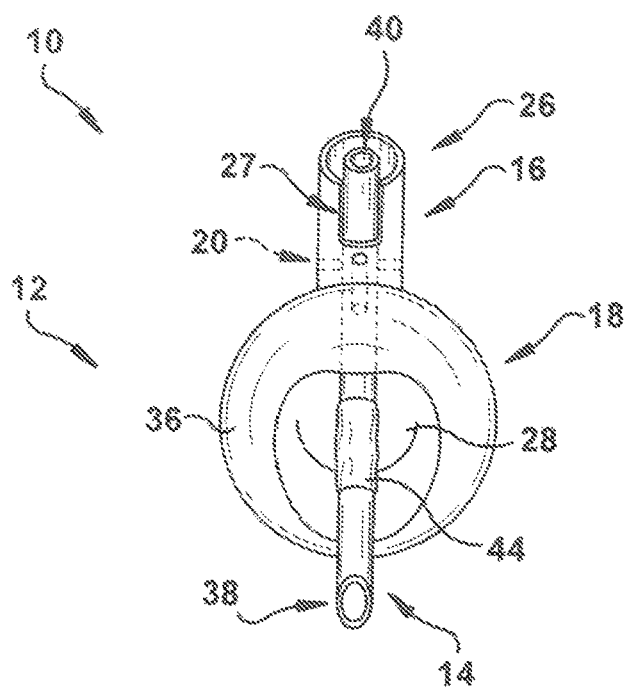
FIG. 2A is a perspective view taken from the top of the airway device in FIG. 1.
Figure 2B:
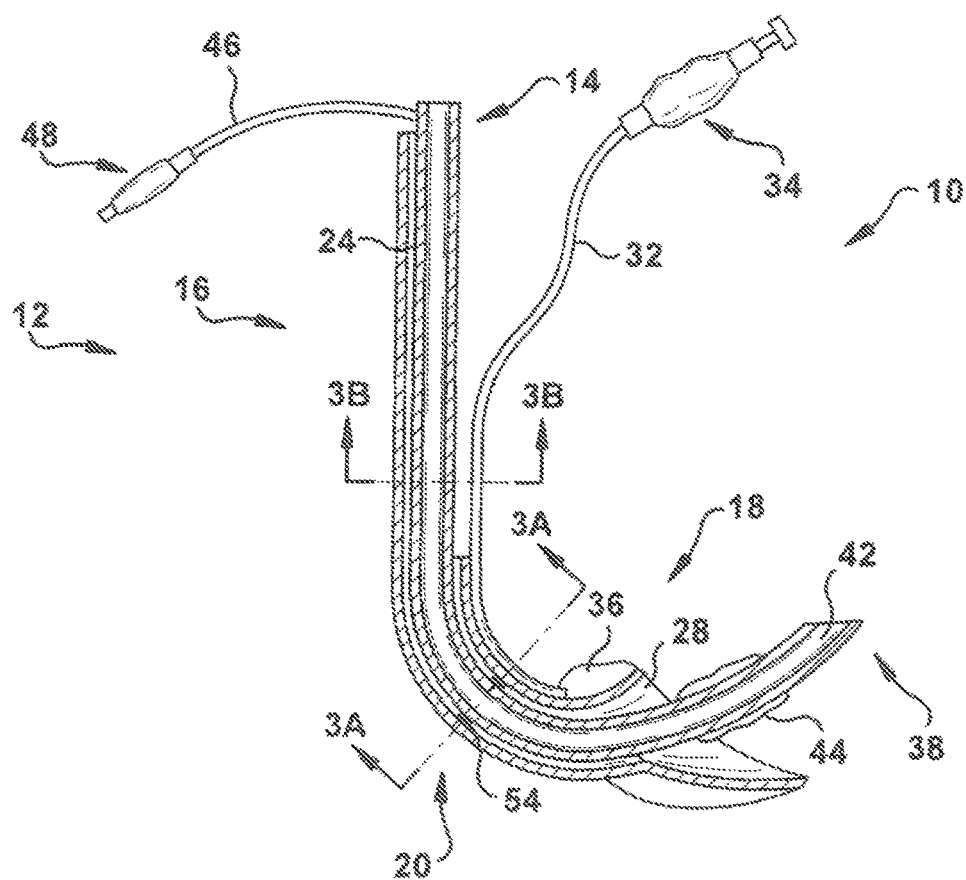
FIG. 2B is a cross-sectional view taken along Line 2B-2B in FIG. 1.
Figure 4A:
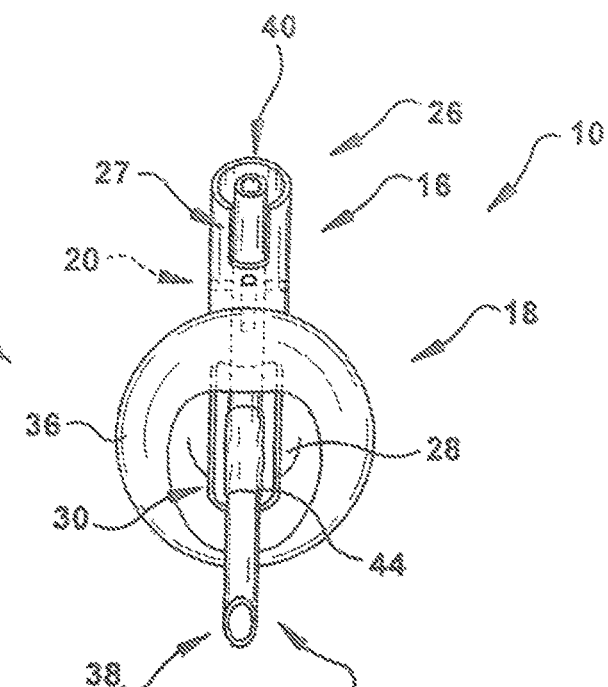
FIG. 4A is a perspective view showing the airway device in FIG. 2A with a guide member attached thereto.
Figure 4B:
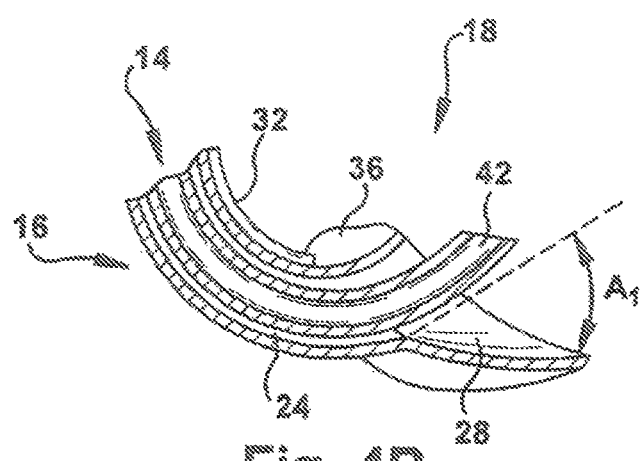
FIG. 4B is a cross-sectional view showing a distal end of the airway device in FIG. 1.
Figure 4C:
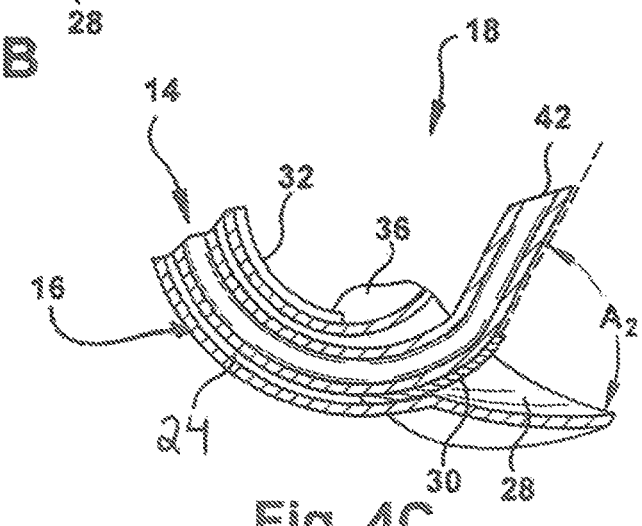
FIG. 4C is a cross-sectional view showing a distal end of the airway device in FIG. 4A.

The laryngeal mask 18 can include an opening 28 in fluid communication with the first passageway 24 (FIGS. 2A-B). In some instances, the opening 28 can be beveled to substantially match the angle of the subject's laryngeal inlet after insertion of the supra-glottic airway support 12 into the subject's airway. In other instances, the laryngeal mask 18 can include a guide member 30 (FIGS. 4A-C) for directing the endotracheal tube 14 at a desired angle (e.g., to substantially match the angle of the subject's laryngeal inlet). The guide member 30 can comprise a piece of plastic, for example, disposed on a surface of the laryngeal mask 18 adjacent the opening 28. In one example, the guide member 30 can have a rectangular shape and include a U-shaped cross-sectional profile. As shown in FIG. 4C, the guide member 30 can be disposed within the distal end portion 22 of the tubular guide 16 and extend partially outward therefrom. The angle $A_2$ formed by virtue of the guide member 30 can be customized depending upon the construction (e.g., length, width, thickness, etc.) of the guide member so that the angle $A_2$ is different from the angle $A_1$ (FIG. 4B), which is naturally formed by the bevel associated with the opening 28 of the laryngeal mask 18.

The supra-glottic airway support 12 can further include an inflation tube 32 (FIG. 1) and an air valve 34 for inflating and deflating an inflatable portion 36 or member (e.g., a cuff) of the laryngeal mask 18. In addition, the supra-glottic airway support 12 can include a central support member (not shown in detail) that is a flexible and somewhat elastic or yielding membranous material, which generally provides support for the laryngeal mask 18. Additionally or optionally, the laryngeal mask 18 can include one or more suction ports (not shown). Each suction port can be in fluid communication with a vacuum or source of negative pressure (not shown). In one example, the laryngeal mask 18 can include one or more suction ports circumferentially spaced about the perimeter of the inflatable portion 36. The suction port(s) can be used to remove secretions or fluid from the patient's airway during use of the airway device 10.

In another aspect, the airway device 10 includes an endotracheal tube 14 that is slidably disposed within the first passageway 24 (FIGS. 2A-B) of the tubular guide 16. By "slidably disposed", it is meant that the endotracheal tube 14 is not fixed within the first passageway 24 so that it is incapable of telescoping through the tubular guide 16. Rather, the term "slidably disposed" can mean that the endotracheal tube 14 is translatable along a longitudinal axis of the first passageway 24 (e.g., using tactile force). In some instances, substantially the entire length of the endotracheal tube 14 can extend through the first passageway 24. The endotracheal tube 14 can be sized and dimensioned to ventilate a patient requiring anesthesia and/or respiratory assistance. In some instances, the endotracheal tube 14 can comprise a plastic tube that can be passed through the supra-glottic airway support 12, past the vocal cords, and lodged in the trachea proximal (or above) the lungs. The endotracheal tube 14 can include a distal end 38, a proximal end 40, and a second passageway 42 that extends between the distal and proximal ends. With the endotracheal tube 14 disposed in the first passageway 24, the second passageway 42 and the first passage way are concentric or coaxial with one another. Since the tubular guide 16 is sized and dimensioned to receive the endotracheal tube 14, a diameter associated with the first passageway 24 can be greater than a diameter associated with the second passageway 42.

The endotracheal tube 14 can include a cuff 44 or balloon portion surrounding the circumference of the endotracheal tube near the distal end 38 that rests in the patient's trachea. The cuff 44 can be inflated to seal against the wall of the trachea after the endotracheal tube 14 has been properly inserted into a subject. Once sealed, positive pressure ventilation may be used to provide respiratory assistance and, if desired, anesthesia or other gas, gas mix, etc., to the patient though the endotracheal tube 14 via a ventilator (not shown). The cuff 38 provides a seal that tends to block liquids and solids from passing along the outside of the endotracheal tube 14 between the tube and trachea wall and entering the patient's lungs. The endotracheal tube 14 can further include an inflation tube 46 (FIG. 1) and an air valve 48 for inflating and deflating the cuff 44.

In another aspect, the airway device 10 includes a sealing mechanism 20 (FIGS. 2A-B) configured to occlude the flow of a gas, gas mix, etc., through the first passageway 24. The sealing mechanism 20 is disposed within a portion of the first passageway 24. The sealing mechanism 20 is configured to permit the endotracheal tube 14 to translate along the longitudinal axis of the tubular guide 16, while simultaneously preventing a gas, gas mix, etc., to flow between the distal and proximal end portions 22 and 26 of the tubular guide. The sealing mechanism 20 is configured to form a fluid-tight seal between an inner surface 50 (FIG. 3B) of the first passageway 24 and an outer surface 52 of the endotracheal tube 14. As discussed in more detail below, the sealing mechanism 20 (FIGS. 2A-B) imparts the airway device 10 with the ability to change from the supra-glottic airway support 12 to an endotracheal tube 14 (and back again) by providing a single, common airway (i.e., the second passageway) that is not disrupted or stopped when the ventilation needs of the patient change.

Figure 3A:
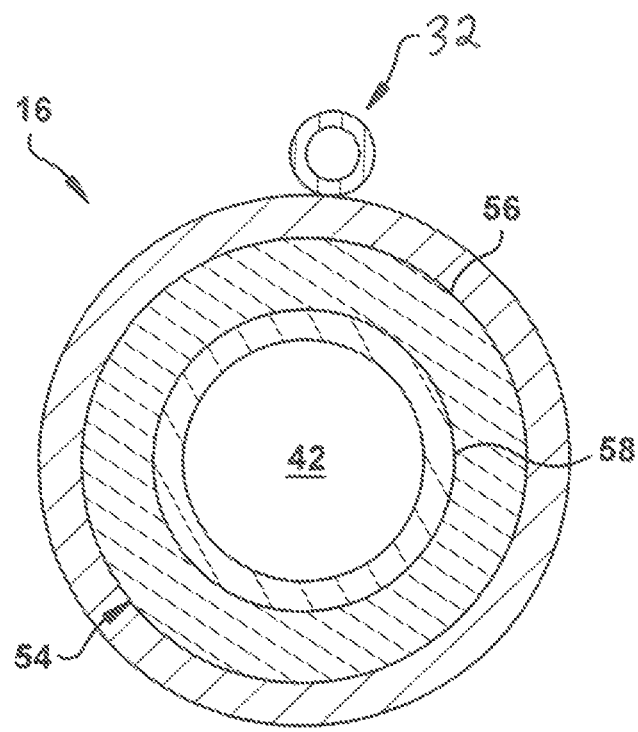
FIG. 3A is a cross-sectional view taken along Line 3A-3A in FIG. 2B.
Figure 3B:
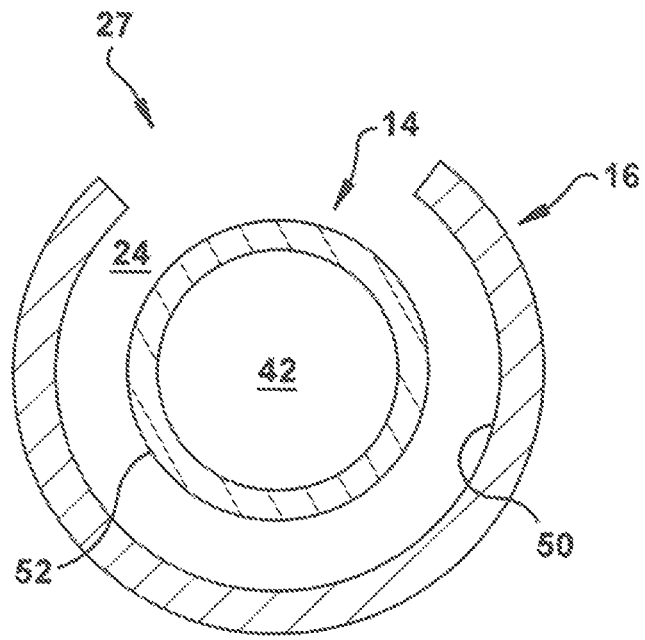
FIG. 3B is a cross-sectional view taken along Line 3B-3B in FIG. 2B.

In some instances, the sealing mechanism 20 can include one or more sealing members 54 configured to directly contact, and encircle, a portion of the outer surface 52 (FIG. 3B) of the endotracheal tube 14. In one example, a sealing member 54 (FIG. 3A) can include an O-ring, a gasket, an inflatable cuff or cushion, or the like. As shown in FIG. 3A, the sealing member 54 can comprise an O-ring having outer and inner circumferential surfaces 56 and 58 that are configured to directly contact the inner surface 50 of the first passageway 24 and the outer surface 52 of the endotracheal tube 14, respectively. By "directly contact", is meant that there are no intervening structures, components, elements, surfaces, etc., between a first structure or surface (e.g., the inner surface 50) and a second structure or surface (e.g., the outer surface 56). Although the sealing member 54 is shown and described as being located at the distal end portion 22 (FIGS. 2A-B) of the tubular guide 16, it will be appreciated that the sealing member can be located at any point within the tubular guide. Additionally, it will be appreciated that two, three, or more sealing members 54 can be used to form the sealing mechanism 20.

Figure 5:
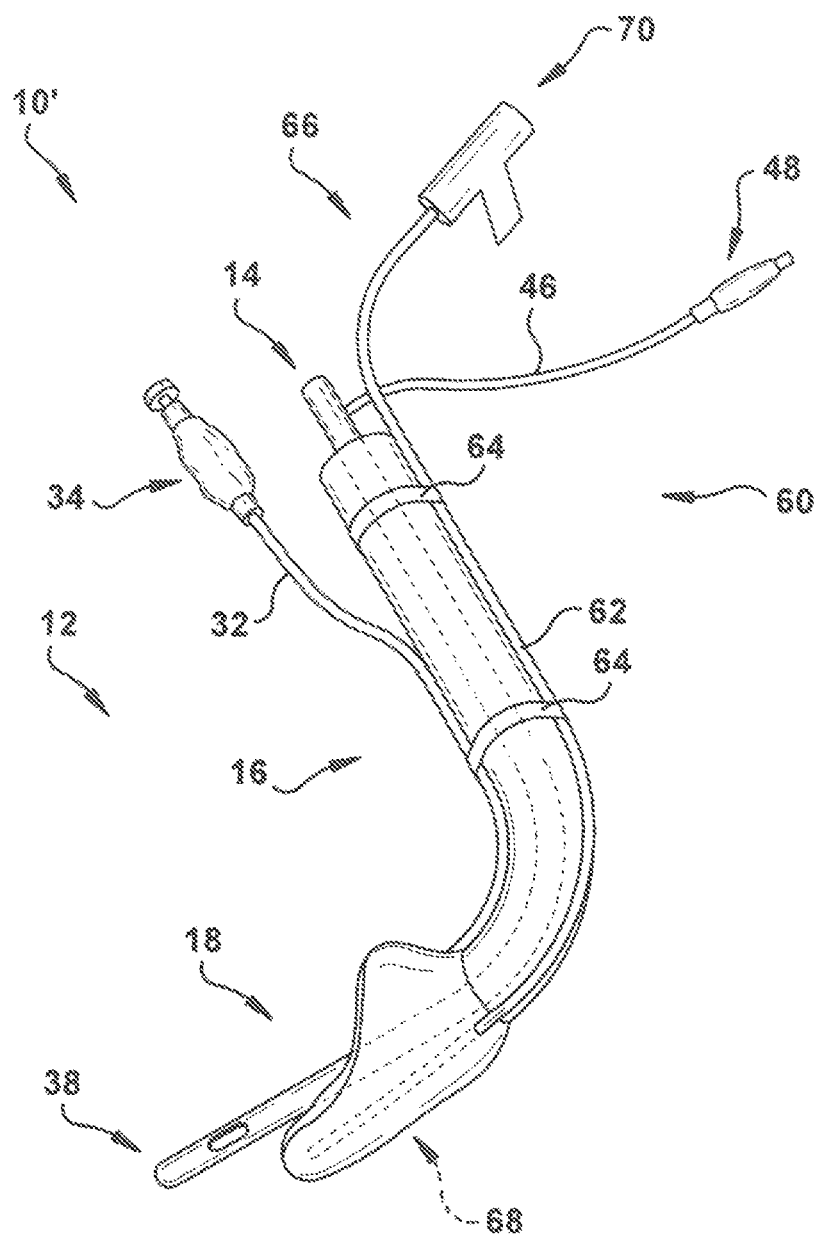
FIG. 5 is a perspective view showing another alternative configuration of the airway device in FIG. 1.

Another aspect of the present disclosure can include a reversible airway device 10' (FIG. 5) that includes a stiffening mechanism 60. Other than the stiffening mechanism 60, the airway device 10' can be identically constructed as the airway device 10 in FIG. 1. The stiffening mechanism 60 can be configured to allow a user to selectively adjust the position of the laryngeal mask 18, for example, when the supra-glottic airway support 12 is implanted in the airway of a subject. As shown in FIG. 5, the stiffening mechanism 60 can be operably coupled to the supra-glottic airway support 12. In one example, the stiffening mechanism 60 can comprise tubing 62 that is securely connected to the tubular guide 16 via a fastening mechanism 64, such as a band, clamp, rivet or other device. A wire (not shown) can extend from a proximal end 66 to a distal end 68 of the tubing 62. The wire can be controllable by a handle 70, which is operably connected to the proximal end 66 of the tubing 62. In use, a user can operate the handle 70 to adjust the tension associated with the wire and thereby control movement of the laryngeal mask 18 during and/or after insertion of the supra-glottic airway support 12 into a subject's airway.

Methods

Figure 6:
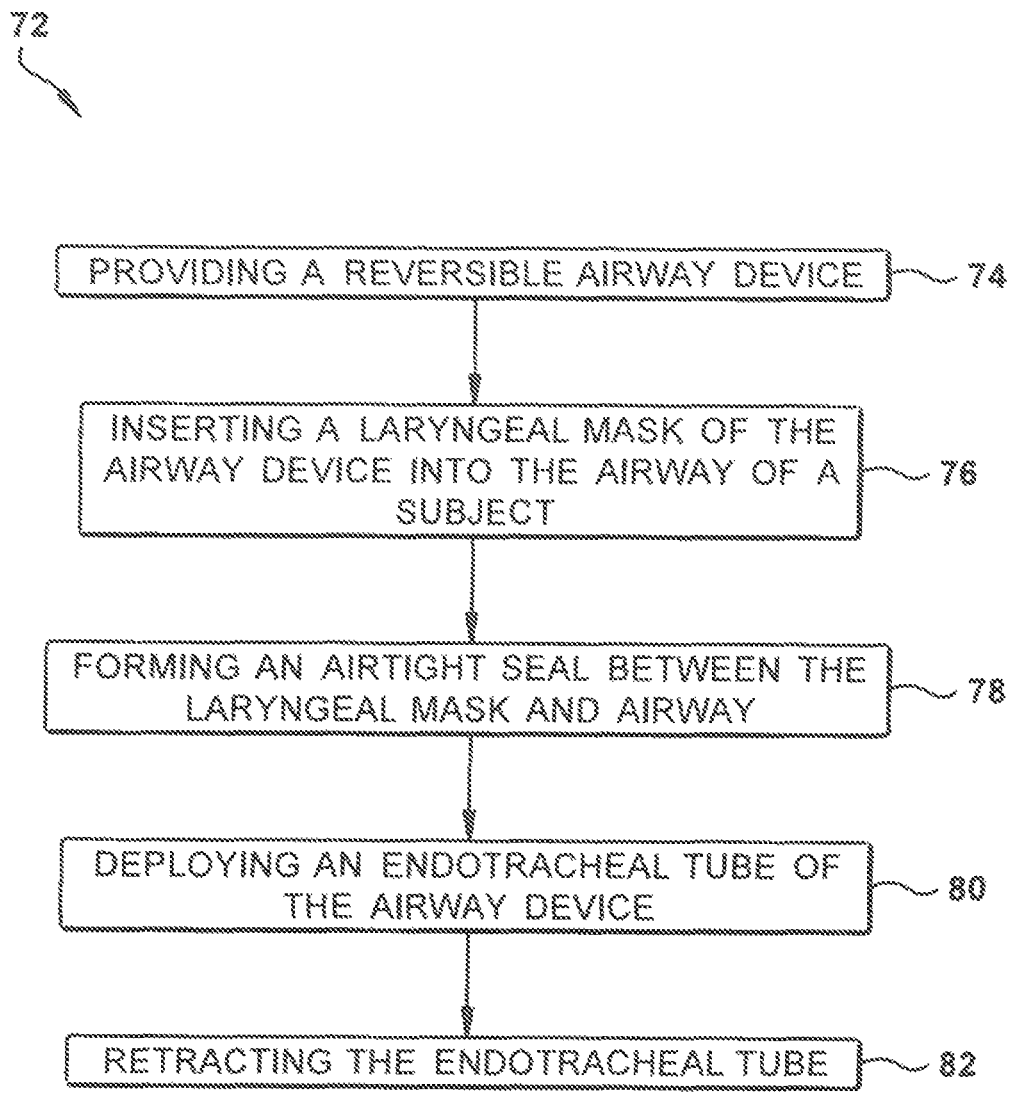
FIG. 6 is a process flow diagram illustrating a method for ventilating a subject according to another aspect of the present disclosure.

Another aspect of the present disclosure includes a method 72 (FIG. 6) for providing an artificial airway in a subject. Although supra-glottic airway devices, such as LMAs, are known as rescue devices that are easy to use in less trained hands, such devices are not a definite airway. Current methods for changing a supra-glottic airway support device to an endotracheal tube involve using different devices; however, such methods risk the danger of disconnection and/or loss of the airway. As described below, the method 72 of the present disclosure advantageously provides a technique for maintaining the airway of a subject while changing between different forms of airway assistance. A high level of skill is not required to perform the method 72, which makes the present disclosure ideal for first responders, EMS personnel, etc., that may need to quickly change from a supra-glottic airway support device to an endotracheal tube (and back) without the requisite level of skill.

Figure 7:
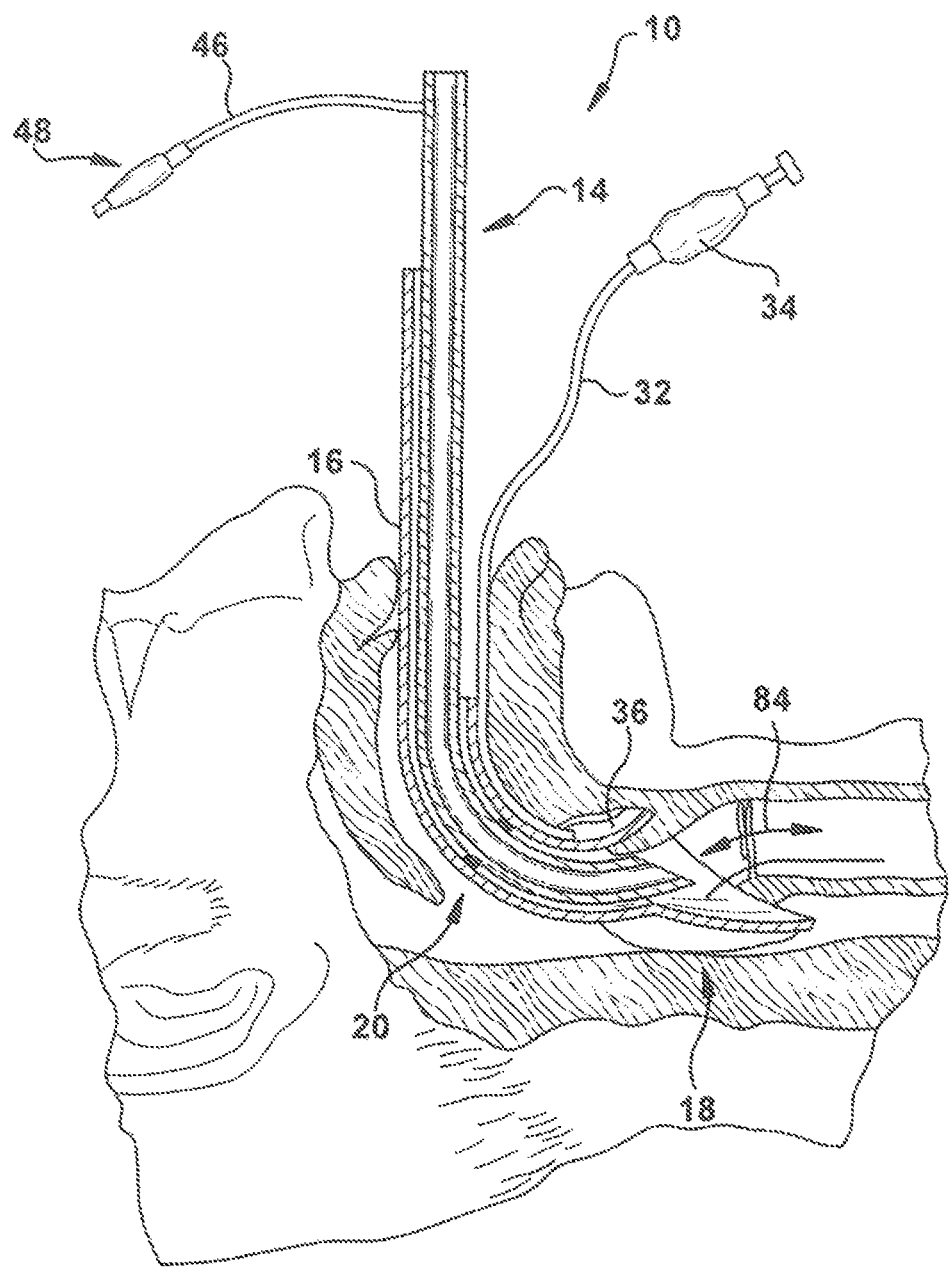
FIG. 7 is a cross-sectional view showing the airway device in FIG. 1 inserted in the airway of a subject.
Figure 8:
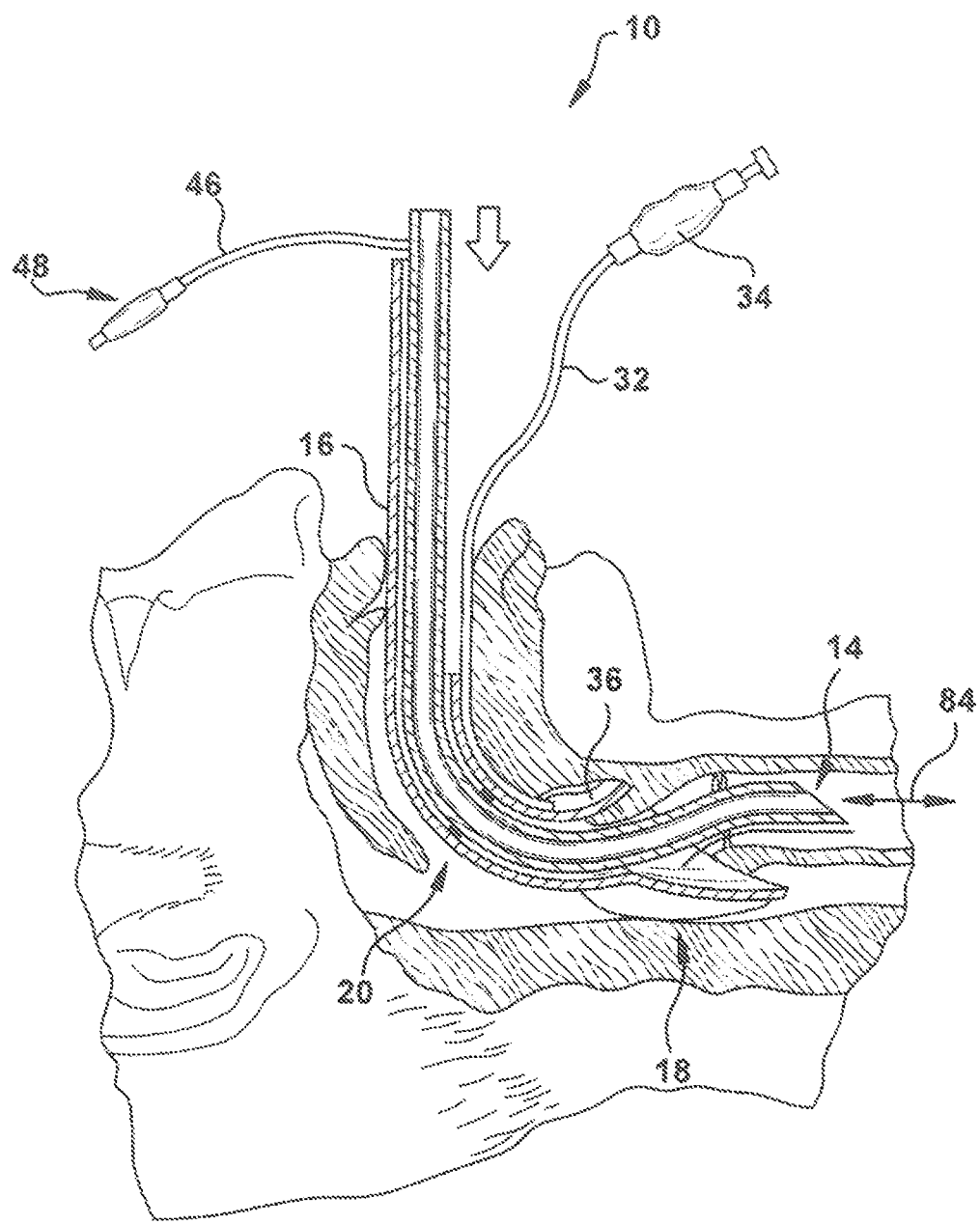
FIG. 8 is a cross-sectional view showing an endotracheal tube of the airway device in FIG. 7 being deployed through the vocal cords of the subject.
Figure 9:
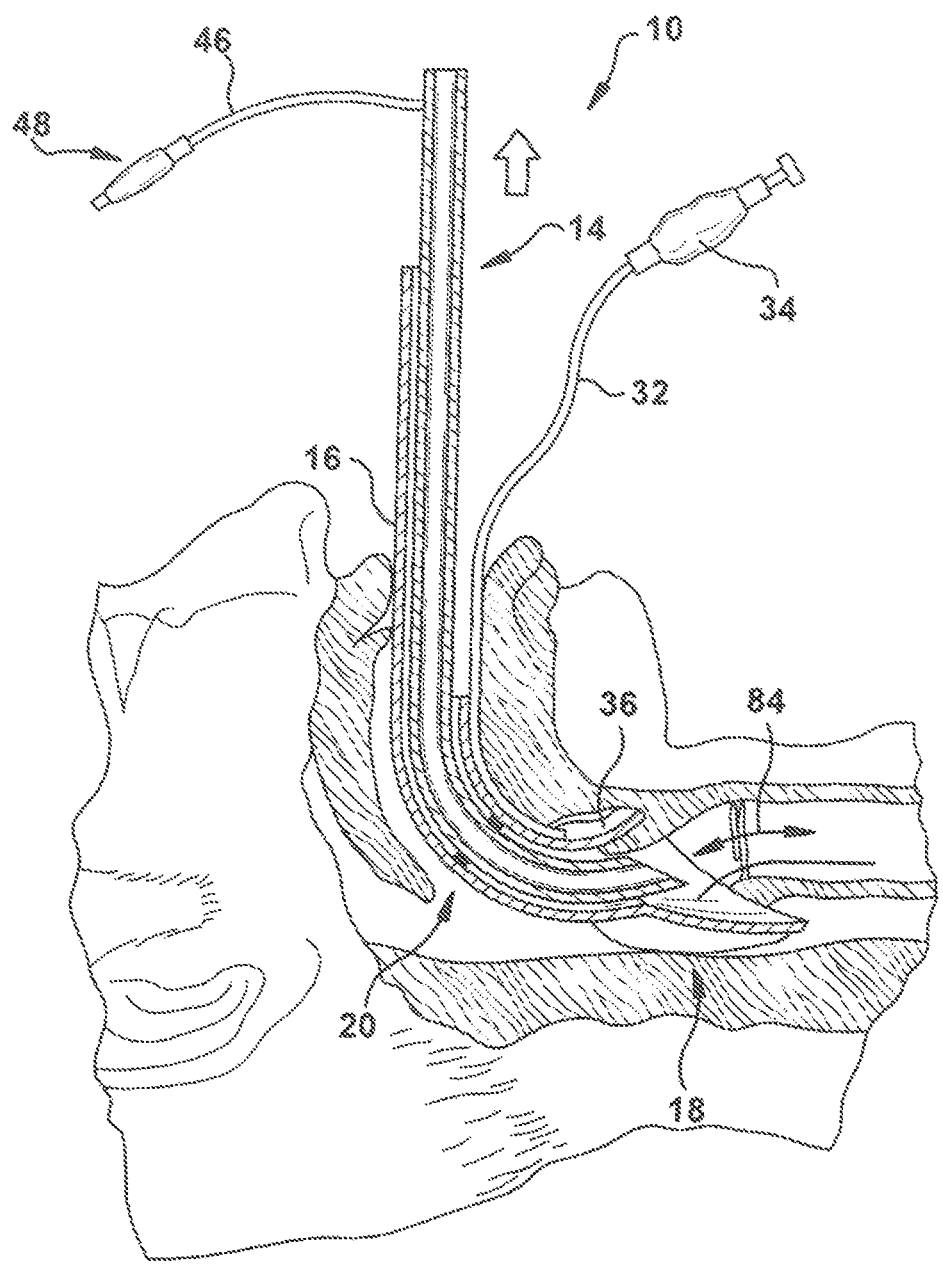
FIG. 9 is a cross-sectional view showing the endotracheal tube in FIG. 8 being retracted from the trachea of the subject.

The method 72 can generally include the steps of providing a reversible airway device 10 (Step 74), inserting a laryngeal mask 18 of the airway device into a subject (Step 76), forming an airtight seal between the laryngeal mask and the airway (Step 78), deploying an endotracheal tube 14 of the airway device (Step 80), and retracting the endotracheal tube (Step 82). Referring to FIGS. 7-9, a patient is shown schematically with the mouth open in cross-section and leading to the back of the throat (sometimes the mouth and/or throat are referred to as the oral cavity of the patient), and from there to the trachea via the laryngeal inlet, which provides an airway that leads to the lungs.

At Step 74, the method 72 can include providing a reversible airway device 10. The reversible airway device 10 can be constructed in an identical or similar manner as shown in FIG. 1 and described above. Alternatively, the airway device 10 can be constructed in an identical or similar manner as the airway device 10' shown in FIG. 5 and described above. For the purpose of illustration only, the method 72 will be described below using the airway device 10 of FIG. 1. It will be appreciated that the airway device 10 can be sized and dimensioned to accommodate a variety of patient sizes, such as pediatric patients.

After selecting an appropriately-sized airway device 10, the laryngeal mask 18 can be inserted into the oral cavity (mouth) of the subject (Step 76). As shown in FIG. 7, the laryngeal mask 18 and its support member can then be positioned in the patient so that a lower portion of the laryngeal mask substantially blocks the esophagus to minimize the risk of regurgitation of stomach contents and the passage of air into the stomach. An upper portion of the laryngeal mask 18 also guides the distal end portion 22 of the tubular guide 16 into alignment using the laryngeal inlet of the patient as a guide to insert along the patient's airway, which is partially represented by the arrow 84.

Once inserted, the inflatable portion 36 of the laryngeal mask 18 can be inflated through the inflation tube 32 so that the upper portion of the laryngeal mask substantially fills the patient's laryngopharynx at the level of the laryngeal inlet. At Step 78, the upper portion of the laryngeal mask 18 surrounds the laryngeal inlet so that the opening 28 of the laryngeal mask is substantially sealed in fluid communication with the laryngeal inlet, e.g., pressing against walls of the oral cavity portions of the patient. Thus, substantially all of the gas inhaled or exhaled by the patient passes through the second passageway 42 of the endotracheal tube 14.

The endotracheal tube 14 of the airway device 10 can then be deployed, if necessary, at Step 80. The endotracheal tube 14 can be deployed automatically or under direct fiberoptic view. As shown in FIG. 8, the proximal end 40 of the endotracheal tube 14 can be urged downward through the tubular guide 16 using, for example, tactile force. As the endotracheal tube 14 is advanced, the distal end 38 emerges from the opening 28 of the laryngeal mask 18 and passes through the vocal cords of the patient until the cuff 44 of the endotracheal tube is positioned distal (below) the vocal cords. Next, the cuff 44 of the endotracheal tube 14 can be inflated to seal against the wall of the trachea. Once sealed, positive pressure ventilation may be used to provide respiratory assistance and, if desired, anesthesia or other gas, gas mix, etc., to the patient though the second passageway 42 of the endotracheal tube 14 via a ventilator.

When intubation with the endotracheal tube 14 is no longer necessary, the cuff 44 can be deflated and the distal end 38 withdrawn into the tubular guide 16 as shown in FIG. 9 (Step 82). Since an airtight seal is still maintained between the laryngeal mask 18 and the laryngeal outlet, ventilation of the patient can continue uninterrupted through the second passageway 42 upon discontinuing ventilation with the endotracheal tube 14. Alternatively, if there is a failure of intubation using the endotracheal tube 14, the airway device 10 can be changed to the supra-glottic airway support 12 without compromising ventilation since the airtight seal is maintained.

From the above description of the present disclosure, those skilled in the art will perceive improvements, changes and modifications. For example, it will be appreciated that order of steps can be changed so that the endotracheal tube 14 is deployed before Step 78 of the method 72. Such improvements, changes, and modifications are within the skill of those in the art and are intended to be covered by the appended claims. All patents, patent applications, and publication cited herein are incorporated by reference in their entirety.

The following is claimed:

1. A reversible airway device comprising:
a tubular guide having a distal end portion, a proximal end portion, and a first passageway extending between the distal and proximal end portions, wherein the tubular guide includes a longitudinal slot partially extending between the distal and proximal end portions thereof when the reversible airway device is configured for ventilation of a patient and when the reversible airway device is configured for intubation of the patient;
a laryngeal mask attached to the distal end portion of the tubular guide, the laryngeal mask including an opening in fluid communication with the first passageway;
an endotracheal tube slidably disposed within the first passageway, the endotracheal tube having a second passageway that is concentric with the first passageway, the longitudinal slot of the tubular guide being sized and dimensioned to receive the endotracheal tube therethrough; and
a sealing mechanism disposed within the first passageway at the distal end portion of the tubular guide and positioned proximate the longitudinal slot, the sealing mechanism being configured to form a fluid-tight seal in the first passageway between the tubular guide and the endotracheal tube so as to occlude a flow of a gas through the first passageway.

2. The airway device of claim 1, wherein the laryngeal mask includes a guide member for directing the endotracheal tube at a desired angle when the endotracheal tube is urged through the opening.

3. The airway device of claim 2, wherein the guide member is disposed on a surface of the laryngeal mask adjacent the opening.

4. The airway device of claim 1, wherein the sealing mechanism includes one or more sealing members that encircle the endotracheal tube.

5. The airway device of claim 1, wherein substantially the entire length of the endotracheal tube is disposed in, and extends through, the first passageway.

6. The airway device of claim 1, wherein a diameter associated with the first passageway is larger than a diameter associated with the second passageway.

7. The airway device of claim 1, wherein at least one of the first and second passageways is flexible.

8. The airway device of claim 1, wherein the longitudinal slot extends axially along the tubular guide such that the proximal end portion of the tubular guide has a non-circular cross-section.

9. The airway device of claim 1, wherein the longitudinal slot extends the entire length of the proximal end portion, but not the distal end portion, of the tubular guide.

10. The reversible airway device of claim 1, wherein the portion of tubular guide having the longitudinal slot has a substantially C-shaped cross section.

11. A reversible airway device comprising:
a tubular guide having a distal end portion, a proximal end portion, and a first passageway extending between the distal and proximal end portions, wherein the tubular guide includes a longitudinal slot partially extending between the distal and proximal end portions thereof when the reversible airway device is configured for ventilation of a patient and when the reversible airway device is configured for intubation of the patient;
a laryngeal mask attached to the distal end portion of the tubular guide, the laryngeal mask including an opening in fluid communication with the first passageway;
an endotracheal tube slidably disposed within the first passageway, the endotracheal tube having a second passageway that is concentric with the first passageway, the longitudinal slot of the tubular guide being sized and dimensioned to receive the endotracheal tube therethrough;
a sealing mechanism disposed within the first passageway at the distal end portion of the tubular guide and positioned proximate the longitudinal slot, the sealing mechanism being configured to form a fluid-tight seal in the first passageway between the tubular guide and the endotracheal tube so as to occlude a flow of a gas through the first passageway; and
a stiffening mechanism operably connected to the laryngeal mask, the stiffening mechanism for selectively adjusting the position of the laryngeal mask relative to the airway of a subject.

12. The airway device of claim 11, wherein the laryngeal mask includes a guide member for directing the endotracheal tube at a desired angle when the endotracheal tube is urged through the opening.

13. The airway device of claim 12, wherein the guide member is disposed on a surface of the laryngeal mask adjacent the opening.

14. The airway device of claim 11, wherein the sealing mechanism includes one or more sealing members that encircle the endotracheal tube.

15. The airway device of claim 11, wherein substantially the entire length of the endotracheal tube is disposed in, and extends through, the first passageway.

16. The airway device of claim 11, wherein a diameter associated with the first passageway is larger than a diameter associated with the second passageway.

17. The airway device of claim 11, wherein at least one of the first and second passageways is flexible.

18. The reversible airway device of claim 11, wherein the portion of tubular guide having the longitudinal slot has a substantially C-shaped cross section.

19. A method for providing an artificial airway in a subject, the method comprising the steps of:

providing a reversible airway device that includes a tubular guide, a laryngeal mask, an endotracheal tube and a sealing mechanism, the tubular guide having a distal end portion, a proximal end portion, and a first passageway extending between the distal and proximal end portions, wherein the tubular guide includes a longitudinal slot partially extending between the distal and proximal end portions thereof when the reversible airway device is configured for ventilation of a patient and when the reversible airway device is configured for intubation of the patient, the longitudinal slot being sized and dimensioned to receive the endotracheal tube therethrough, the laryngeal mask being attached to the distal end portion and including an opening in fluid communication with the first passageway, the endotracheal tube being slidably disposed within the first passageway and having a second passageway that is concentric with the first passageway, the sealing mechanism being disposed in the first passageway at the distal end portion of the tubular guide and positioned proximate the longitudinal slot, the sealing mechanism forming a fluid-tight seal in the first passageway between the tubular guide and the endotracheal tube;

inserting the laryngeal mask into the subject so that an airtight seal is formed between the laryngeal mask and the airway of the subject;

deploying the endotracheal tube so that a distal end of the endotracheal tube is positioned below the vocal cords of the subject; and retracting the endotracheal tube so that the distal end of the endotracheal tube is positioned above the vocal cords;

wherein a flow of a gas through the second passageway is uninterrupted during the inserting and deploying steps.

20. The method of claim 19, wherein the inserting step further includes adjusting the position of the laryngeal mask relative to the airway of the subject using a stiffening mechanism that is operably connected to the laryngeal mask.

21. The method of claim 19, wherein the sealing mechanism allows the gas to flow through the second passageway when the airtight seal is formed.

22. The method of claim 19, wherein the portion of tubular guide having the longitudinal slot has a substantially C-shaped cross section.

\* \* \* \* \*